US00PP24439P3

(12) United States Plant Patent
Cain

(10) Patent No.: US PP24,439 P3
(45) Date of Patent: May 13, 2014

(54) GRAPEVINE 'IFG FOUR'

(50) Latin Name: *Vitis vinifera*
Varietal Denomination: IFG Four

(75) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 13/134,949

(22) Filed: Jun. 22, 2011

(65) Prior Publication Data

US 2012/0331598 P1 Dec. 27, 2012

(51) Int. Cl.
*A01H 5/00* (2006.01)

(52) U.S. Cl.
USPC ..... Plt./205

(58) Field of Classification Search
CPC ..... A01H 5/0812
USPC ..... Plt./205
See application file for complete search history.

(56) References Cited

U.S. PATENT DOCUMENTS

PP16,229 P2 1/2006 Ramming et al.

*Primary Examiner* — Annette Para

(57) ABSTRACT

A new and distinct grapevine variety denominated 'IFG Four' is characterized by producing large, very crisp, dark red, uniform berries with high sugar content borne on medium to large size clusters. The fruit ripen and are commercially harvestable from mid to late August.

1 Drawing Sheet

Latin name of the genus and species claimed: *Vitis vinifera*. Variety denomination: 'IFG Four'.

BACKGROUND OF THE INVENTION

The new and distinct grapevine described and claimed herein originated from a hand pollinated cross of the Autumn Royal variety (non-patented) and the Crimson variety (non-patented) hybridized in May 2001. The abortive seed traces were subsequently embryo cultured and the resulting plant was planted in the field in April 2002. The present variety of grapevine was selected as a single plant in July 2003 and was first asexually propagated by hardwood cuttings in December 2003 near Delano, Kern County, Calif. The resulting propagules were planted during April 2004 near Delano, Kern County, Calif. and were found to reproduce true-to-type through at least three generations of asexual reproduction.

BRIEF SUMMARY OF THE INVENTION

The new grapevine 'IFG Four' is characterized by producing naturally large, extremely crisp, elongated dark red seedless berries that require little or no exogenous application of Gibberellic acid to obtain commercially acceptable berry size which ripen in mid-season.

To the inventor's knowledge, the known variety to which the new grapevine variety is most similar is the Scarlet Royal (U.S. Plant Pat. No. 16,229). It can be distinguished from this variety based on unique combination of characteristics, which include naturally larger, more crisp, very uniform berries. Berries of IFG Four are more elongated than Scarlet Royal. Natural berry weight is slightly larger and is substantially larger with the application of Gibberellic acid. Acidity of 'IFG Four' is lower than that of Scarlet Royal at a given sugar level. Productivity of 'IFG Four' is somewhat lower than Scarlet Royal. 'IFG Four' can further be distinguished based on the characteristics described below.

BRIEF DESCRIPTION OF THE FIGURE

The accompanying photographic illustration in FIG. 1 illustrates in full color 'IFG Four'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Four' plants grown in the vicinity of Delano, Kern County, Calif. during 2009 and 2010, and is believed to apply to plants of the variety grown under similar conditions of soil and climate elsewhere:

VINE

General:

*Size*.—Large.

*Vigor*.—Vigorous.

*Density of foliage*.—Dense.
*Productivity*.—Medium productive.
*Root stock*.—Own root.
*Training method*.—Typically spur pruned leaving 2 bud spurs.

Trunk:
*Trunk diameter of 4-year-old vines at 30 cm above the soil line*.—6.7 cm.
*Shape*.—Stocky.
*Straps*.—Short — Split.
*Surface texture*.—Shaggy.
*Inner bark color*.—Greyed orange; 165A.

SHOOTS

Young shoot:
*Form of tip*.—Wide open.
*Distribution of anthocyanin coloration of tip*.—Piping (striped).
*Intensity of anthocyanin coloration of tip*.—Weak.
*Density of prostrate hairs of tip*.—Dense.
*Density of erect hairs of tip*.—Absent.
*Color*.—Can be any of the following colors; Green 144A, and 146B.

Woody shoot (mature canes):
*Shape*.—Medium.
*Internode length*.—Medium; About 11.3 cm.
*Width at node*.—About 1.3 cm.
*Cross section*.—Elliptic.
*Surface*.—Smooth.
*Main color*.—Can be any of the following colors; Yellowish brown; 165B, and 174B.
*Density of erect hairs of nodes*.—None or very sparse.
*Density of erect hairs on internodes*.—None or very sparse.
*Growth of axillary shoots*.—Strong; Approximately 30.6 cm.

Flowering shoot:
*Vigor during flowering*.—Strong.
*Attitude during flowering on shoots not tied*.—Semi-erect.
*Color*.—Dorsal side of internodes — Green — Green with Red stripes.
*Color*.—Ventral side of internodes — Green.
*Color*.—Dorsal side of nodes — Green with Red stripes.
*Color*.—Ventral side of nodes — Green; 144A.
*Density of prostrate hairs of nodes*.—Sparse.
*Density of erect hairs of nodes*.—None.
*Density of prostrate hairs on internode*.—Very sparse.
*Density of erect hairs on internode*.—None.
*Anthocyanin coloration of buds*.—Absent.

Tendrils:
*Distribution on the shoot (at full flowering)*.—Discontinuous.
*Length of tendril*.—Medium — Long; About 20.9 cm.
*Thickness*.—Medium.
*Color*.—N144A.
*Form*.—Bifurcated to Trifurcated.
*Number of consecutive tendrils*.—2.

LEAVES

Young leaves:
*Color of upper surface of first four distal unfolded leaves*.—Copper yellow.
*Average intensity of anthocyanin coloration of six distal leaves prior to flowering*.—Weak — Medium.
*Density of prostrate hairs between veins (lower surface)*.—Very sparse.
*Density of prostrate hairs on veins (lower surface)*.—Medium.
*Density of erect hairs between veins (lower surface)*.—Absent.
*Density of erect hairs on veins (lower surface)*.—Sparse.

Mature leaves:
*Average length*.—About 13.9 cm.
*Average width*.—About 16.9 cm.
*Mature leaf size*.—Large.
*Shape of blade*.—Pentagonal.
*Number of lobes*.—5.
*Anthocyanin coloration of main veins on upper side of blade*.—Absent.
*Mature leaf profile*.—Flat.
*Blistering surface of blade upper surface*.—Weak.
*Leaf blade tip*.—In the plane of the leaf.
*Undulation of margin*.—Slight.
*Thickness*.—Medium.
*Undulation of blade between main and lateral veins*.—Only near petiole.
*Shape of teeth*.—Mixture of both sides straight and both sides convex.
*Length of teeth*.—Medium.
*Ratio length/width of teeth*.—Equal.
*Shape of upper lateral sinuses*.—Closed.
*Depth of upper lateral sinuses*.—Medium.
*General shape petiole sinus*.—Slightly open to Closed.
*Shape of base of upper leaf sinuses*.—V-shaped.
*Tooth at petiole sinus*.—Absent.
*Density of prostrate hairs between veins on lower surface of blade*.—Very sparse.
*Density of erect hairs between veins on lower surface of blade*.—Absent.
*Density of prostrate hairs on main veins on lower surface of blade*.—Sparse-Medium.
*Density of erect hairs on main veins on lower surface of blade*.—Medium.
*Density of prostrate hairs on main veins on upper surface of blade*.—Sparse.
*Density of erect hairs on main veins on upper surface of blade*.—None or very sparse.
*Autumn coloration of leaves*.—Leaves can be a single color or combination of colors, in a mottled pattern or on the edges of the leaves; Yellow 11A, and Yellow-green 153A, and C, and D, and Grey-purple 183A, and B.

Upper surface:
*Color*.—Can be any of the following colors; 137A, and B.
*Anthocyanin coloration of main veins*.—Absent.
*Surface appearance*.—Semi-glossy.
*Blistering surface of blade*.—Very weak.

Lower surface:
*Color*.—Can be any of the following colors; 146A, and B.
*Anthocyanin coloration of main veins (lower surface)*.—Absent.
*Glossiness*.—Medium.
*Surface texture*.—Smooth.
*Surface appearance*.—Semi-glossy.

Petiole:

*Length*.—About 15.4 cm.

*Length of petiole compared to middle vein*.—Slightly shorter — Equal.

*Density of prostrate hairs on petiole*.—Sparse.

*Density of erect hairs on petiole*.—None.

Buds:

*Bud fruitfulness*.—Basal: Mostly fruitful.

*Position of first fruitful shoot on previous season cane*.—$2^{nd}$ to $3^{rd}$ node Time of bud burst — Late; Mar. 17, 2010.

FLOWERS

General:

*Flower sex*.—Hermaphrodite.

*Length of first inflorescence*.—Medium; About 13.6 cm long by 8.0 cm wide.

*Position of first flowering and fruiting node*.—$3^{rd}$ to $5^{th}$ node (current season growth).

*Number of inflorescence per flowering shoot*.—1.1.

*Time of bloom*.—Late as compared with similar varieties in the growing area of Delano, Calif.

*Date of full bloom*.—May 22, 2010.

FRUIT

General:

*Ripening period*.—Mid — late; Approximately August 20 in a typical year.

*Use*.—Fresh market.

*Keeping quality*.—Medium.

*Resistance to*.—Insects: Average typical of *Vitis vinifera* species. Diseases: Average typical of *Vitis vinifera* specie.

*Shipping quality*.—Medium.

*Refractometer test*.—Soluble-sugar: About 18.4 Brix.

*Brix/acid*.—About 47.6.

*Titratable acidity*.—About 0.39.

*Juice pH*.—About 4.2.

Cluster:

*Mature cluster length* (*peduncle excluded*).—About 32.6 cm.

*Mature cluster width*.—About 13.7 cm.

*Mature cluster weight*.—About 802 gm.

*Bunch density*.—Loose.

*Number of berries*.—About 165.

*Form*.—Cylindrical.

Peduncle:

*Lignification of peduncle*.—Weak — Medium.

*Length of peduncle*.—Approximately 3.9 cm.

Berry:

*Uniformity of size*.—Uniform.

*Single berry weight*.—About 6.0 g natural; to about 9.1 g when treated with gibberellic acid.

*Shape*.—Oblong.

*Seeds*.—Contains small rudimentary seed traces.

*Cross section*.—Circular.

*Berry dimensions*.—Longitudinal axis: About 26.8 mm horizontal axis: About 18.6 mm.

*Berry firmness*.—Firm.

*Particular flavor*.—Neutral.

*Bloom* (*cuticular wax*).—Medium thick.

*Berry separation from pedicel*.—Medium difficult.

*Skin color* (*without bloom*).—Red — purple; 59A.

Skin:

*Thickness*.—Thin.

*Texture*.—Medium tough.

*Reticulation*.—Absent.

*Tenacity*.—Tenacious to flesh.

*Tendency to crack*.—Occasional cracks at pedicel.

What is claimed:

1. A new and distinct variety of grapevine as herein illustrated and described.

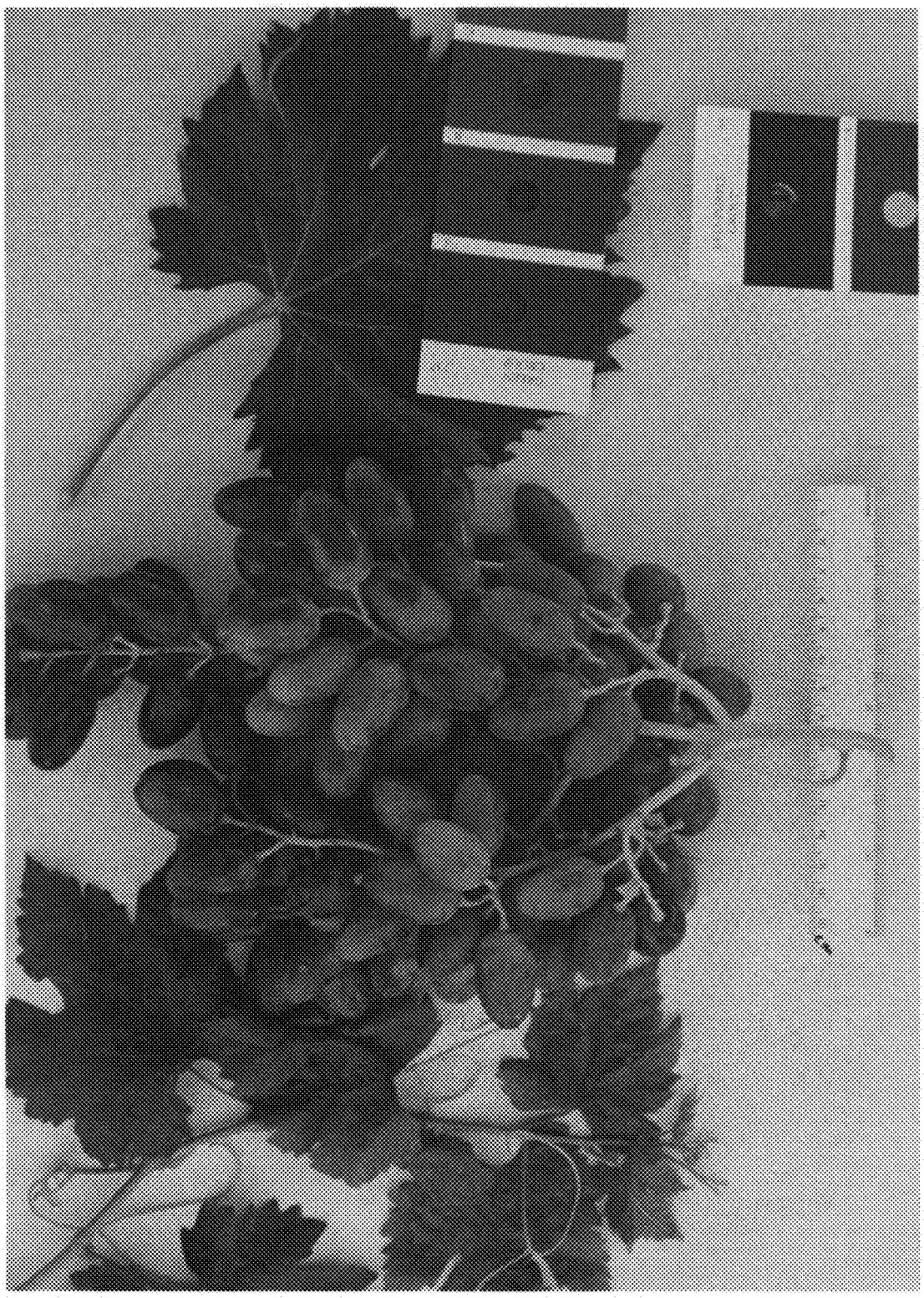

* * * * *